US009528215B2

(12) United States Patent
Tumini et al.

(10) Patent No.: US 9,528,215 B2
(45) Date of Patent: Dec. 27, 2016

(54) APPARATUS, METHOD AND SYSTEM FOR PROVIDING AN AUXILIARY FLUSH TO A CENTRAL CHEMICAL DISPENSING SYSTEM

(71) Applicant: Ecolab USA Inc., St. Paul, MN (US)

(72) Inventors: Jessica Tumini, Crystal, MN (US); Quang Dao, Eden Prairie, MN (US); Adrian Hartz, Woodbury, MN (US); Jon Yurik, Woodbury, MN (US); Gerold Carlhoff, Toenisvorst (DE); Thomas Fassbender, Neuss (DE)

(73) Assignee: Ecolab USA Inc., St. Paul, MN (US)

(*) Notice: Subject to any disclaimer, the term of this patent is extended or adjusted under 35 U.S.C. 154(b) by 0 days.

(21) Appl. No.: 14/481,601

(22) Filed: Sep. 9, 2014

(65) Prior Publication Data

US 2016/0067660 A1 Mar. 10, 2016

(51) Int. Cl.

| | |
|---|---|
| ***A61L 2/00*** | (2006.01) |
| ***B67D 5/06*** | (2006.01) |
| ***E03C 1/10*** | (2006.01) |
| ***D06F 39/02*** | (2006.01) |
| *B01F 15/02* | (2006.01) |
| *B01F 5/02* | (2006.01) |
| *B01F 1/00* | (2006.01) |
| *D06F 33/02* | (2006.01) |

(52) U.S. Cl.

CPC ............ *D06F 39/02* (2013.01); *D06F 39/022* (2013.01); *B01F 1/0027* (2013.01); *B01F 5/02* (2013.01); *B01F 15/0297* (2013.01); *D06F 33/02* (2013.01); *D06F 2204/02* (2013.01)

(58) Field of Classification Search

CPC ....... A61L 2/00; A61K 2300/00; A24F 47/008
USPC .. 422/28, 105, 119, 256, 261, 292; 222/145, 222/144.5, 133, 135, 642; 137/217
See application file for complete search history.

(56) References Cited

U.S. PATENT DOCUMENTS 4,691,850 A 9/1987 Kirschmann
4,845,965 A 7/1989 Copeland et al.
(Continued)

FOREIGN PATENT DOCUMENTS

WO WO2006094219 9/2006
WO WO2011017499 2/2011
WO EP2581486 4/2013

*Primary Examiner* — Monzer R Chorbaji
(74) *Attorney, Agent, or Firm* — Merchant & Gould P.C.

(57) ABSTRACT

Systems and methods for supplying a variety of chemical products to a plurality of utilization points such as to washer extractors or washing machines includes utilizing an auxiliary flush mechanism that operates independently of a product supplying manifold so that the wash machines may be flushed in order to free the manifold to supply product to an otherwise waiting washing machine. The flush mechanism includes flush lines associated with respective washing machines and each line having an auxiliary flush valve and associated flow sensor which are configured to flush water through delivery lines leading to respective washing machines. The systems are configured such that a flushing of a washing machine or machines may occur while product is being supplied to a different washing machine via the central supplying manifold. A programmable controller is included with the system to control the various functions including receiving data from sensors and operating valves and pumps in accordance with the disclosed methods.

21 Claims, 6 Drawing Sheets

(56) References Cited

U.S. PATENT DOCUMENTS

| | | | | |
|---|---|---|---|---|
| 5,435,157 | A | 7/1995 | Laughlin | |
| 5,746,238 | A * | 5/1998 | Brady | B01F 3/088 137/101.19 |
| 6,240,953 | B1 | 6/2001 | Laughlin et al. | |
| 7,845,361 | B1 | 12/2010 | Verespej et al. | |
| 7,931,032 | B1 | 4/2011 | Penkauskas et al. | |
| 2001/0042557 | A1 | 11/2001 | Moh | |
| 2003/0009428 | A1 | 1/2003 | Barbe | |
| 2004/0083771 | A1 | 5/2004 | Simmons | |
| 2005/0072195 | A1 | 4/2005 | McEachern | |
| 2011/0077144 | A1 | 3/2011 | Jessen et al. | |
| 2012/0103364 | A1 | 5/2012 | Monsrud et al. | |
| 2012/0266389 | A1 | 10/2012 | Ihne et al. | |
| 2013/0180293 | A1 | 7/2013 | Huerth et al. | |

* cited by examiner

APPARATUS, METHOD AND SYSTEM FOR PROVIDING AN AUXILIARY FLUSH TO A CENTRAL CHEMICAL DISPENSING SYSTEM

BACKGROUND

Central chemical dispensing systems include designs which dispense a variety of chemicals to multiple devices. In some cases a central dispensing system will dispense chemicals by pumping the different chemicals into a flush line. The flush line provides the chemicals to different devices, or utilization points, such as to different washing machines. The central system will pre-flush the flush line by sending water or other liquid through the flush line. The system will also post-flush the flush line to ensure the chemical or chemicals have been completely delivered to the device or washing machine and to avoid cross-contamination with subsequent chemical dispenses. In a central dispensing system the flush line is split or diverted to various devices or washers (or utilization points) by using a manifold which includes separate valves dedicated to allow flow to separate delivery lines for each device or washer. Some examples of dispensing systems include those found in patents such as U.S. Pat. Nos. 4,691,850 and 5,746,238. While these patented systems and other systems may have useful features, there is room for improvement.

SUMMARY OF THE INVENTION

In one aspect the invention pertains to an apparatus, method and system of providing an auxiliary flush to each delivery line which leads to the utilization point, device or washer of a central dispensing system. The time lapse used to complete a main flush of a central dispensing system can be shortened by use of the auxiliary flush configuration. The auxiliary flush provides an additional flush inlet valve on each washer line. Instead of relying on the flush manifold to flush or completely flush a first washer by flushing through an associated first washer delivery line, a washer product control valve associated with the first washer is closed in order to allow a different washer product control valve associated with a second or subsequent washer to be opened. The auxiliary flush line is configured to complete the flush of the first washer by delivering water through the first delivery line.

In accordance with an aspect of the invention, a central dispensing system includes an inlet manifold configured to receive a variety of chemical products and an outlet manifold in communication with the inlet manifold and in fluid communication with multiple washers via respective delivery lines, the system further including an auxiliary flush line, independent of the manifolds, and configured to provide water to flush the respective delivery lines. Independently flushing the delivery lines allows the system and manifolds to simultaneously supply chemical products to one device while flushing another device, which reduces wait time. The auxiliary flush line may diverge into separate flush lines to flush respective delivery lines, and each auxiliary flush line may include a separate valve and sensor. A controller is configured to control the operation of the system.

In a further aspect of the invention, a central dispensing system includes a receptor or manifold configured to receive a variety of chemical products to mix and deliver to multiple washers via respective delivery lines, the system further including an auxiliary flush line, independent of the manifold, and configured to provide water to flush the respective delivery lines.

In a further aspect of the invention, a controller is configured to control the operation of the system, including the sensing and recording of data and opening/closing of valves, activation of pumps, and timing of the operations, together with providing associated warnings, safety checks and historical data. The controller includes logic circuits, storage medium, a processor, and other electrical arrangements for such controlling of the system.

In a further aspect the invention includes a method of dispensing a variety of fluid products to multiple washers in a central dispensing system having a manifold configured to receive a variety of liquid products and having product control valves which open to allow the liquid product to flow to the manifold and in turn flow to respective multiple washers, the method includes dosing a first washer with a chemical product received from the manifold, and after the dosing of the first washer, flushing the first washer with water from an auxiliary flush line independent of the manifold while simultaneously dosing a second washer with a chemical product received from the manifold.

In a further aspect the invention includes a method of dosing a first washer with a chemical product received from a manifold, and after dosing of the first washer, flushing the first washer with water from an auxiliary flush line independent of the manifold while also flushing a second washer using the auxiliary flush line.

The above partial summary of the present invention is not intended to describe each illustrated embodiment, aspect, or every implementation of the present invention. The figures and detailed description and claims that follow more particularly exemplify these and other embodiments and further aspects of the invention.

BRIEF DESCRIPTION OF THE DRAWINGS

The invention may be more completely understood in consideration of the following description of various embodiments of the invention in connection with the accompanying drawings, in which.

Figure 1:
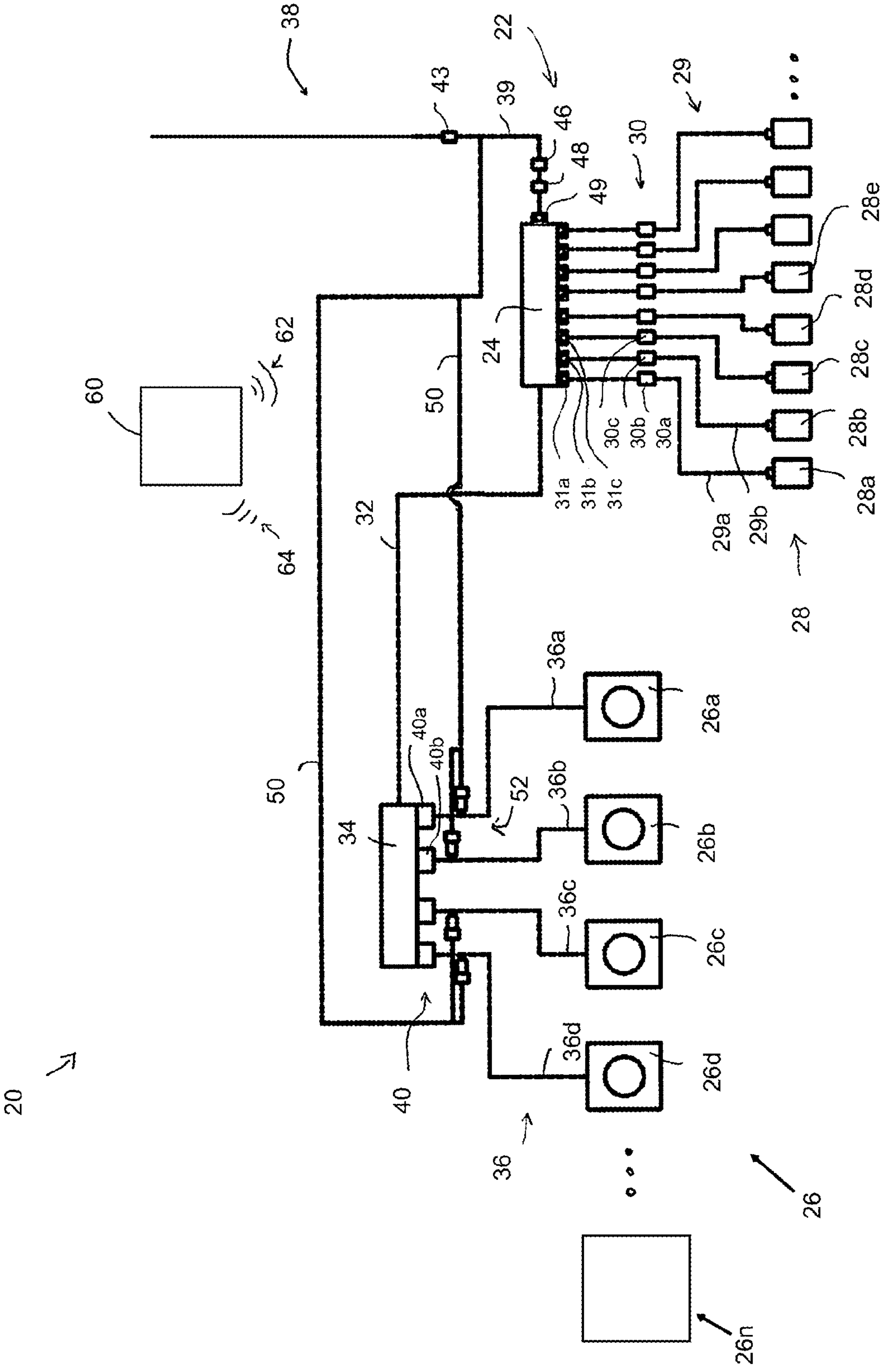
FIG. 1 illustrates schematically the arrangement of a central dispensing system in accordance with the present invention.

While the invention is amenable to various modifications and alternative forms, specifics thereof have been shown by way of example in the drawings and will be described in detail. It should be understood, however, that the intention is not necessarily to limit the invention to the particular embodiments, aspects and features described. The intention is to cover all modifications, equivalents, and alternatives falling within the spirit and scope of the invention and as defined by the appended claims.

DETAILED DESCRIPTION OF THE INVENTION

Referring to FIGS. 1-6, aspects of the central dispensing system and methods according to the present invention are shown. Central dispensing system 20 generally includes a centralized product mixing component 22 which supplies product to a plurality of utilization points such as a plurality of washing machines 26 (26*a*, 26*b*, 26*c*, 26*d*, etc.). In one aspect washing machines 26 include laundry washing machines or washer extractors. Mixing component 22 includes a plurality of product sources 28 (28*a*, 28*b*, 28*c*, 28*d*, etc.). Product supply pumps 30 (30*a*, 30*b*, 30*c*, etc.) draw products (often liquid products) from product sources 28 into a flush manifold or inlet manifold 24. As used herein, "inlet manifold" may include any apparatus that facilitates convergence of water and chemicals or products. In one aspect the inlet manifold 24 communicates with an outlet manifold 34 through a transport line 32. The outlet manifold 34 in turn delivers the products to washers 26 via delivery lines 36 (36*a*, 36*b*, 36*c*, 36*d*, etc). System 20 also includes a supplemental or an auxiliary flush mechanism as described below.

In general, fluid, concentrate, dissolved chemicals, slurry or other product from a product source such as source 28*a* (or multiple product sources 28) is pumped to inlet manifold 24 where it is mixed with water from a water supply 38 and delivered to outlet manifold 34 where it is delivered to a washer 26*a* (or other washers 26). Any number of products may be pumped from the various product sources 28 to be delivered to a washer 26. A nonexclusive list of products that are stored at sources 28 include chemical concentrates which may be delivered to the washers 26, and may include a detergent or detergents, a fabric softener or softeners, a bleach or bleaches, a souring agent or agents, a fragrance, or other chemical product or products. In some applications the product may be dissolved solid products mixed with water. The products are often highly concentrated and diluted when mixed together or mixed with water at inlet manifold 24. It may be appreciated that a variety of combinations of products (or use of single products) may be used and may vary from application to application.

It may be appreciated that the products may not be compatible with each other. Thus, it is typically required to provide a flush of the chemical products to ensure the chemicals have been completely delivered to the machine or machines 26 and to avoid cross-contamination with subsequent chemical deliveries. One way to flush the chemical products from the system is to pass water through inlet manifold 24, through line 32, through outlet manifold 34, through lines 36 and into washers 26. A pre-flush action may be utilized prior to product dosing or dispensation from product sources 28 to assure the system is devoid of non-compatible product. A post-flush action may also be utilized after product dosing or dispensation from product sources 28 and delivery to washer 26.

In a typical central dispensing system it may be appreciated that only one washing machine 26 at a time receives chemical product. For instance, product control valves 40 control the release of fluid and product from outlet manifold 34. Particularly, product control valve 40*a* will open to allow flow of product to delivery line 36*a* and in turn the flow of product to washing machine 26*a*. While valve 40*a* is open, all other product control valves 40 are closed. In this manner it will be possible to determine that all of the product released from inlet manifold 24 will be delivered to the desired washing machine 26*a*. Otherwise, if more than one control valve 40 is able to open simultaneously, the product would likely flow to more than one washing machine 26 and it would be unknown how much of the desired product was or is delivered to which machine 26. In a typical central dispensing system, the flushing of delivery lines 36, such as line 36*a*, is accomplished by passing water through inlet manifold 24, through outlet manifold 34, through an open product control valve 40, such as valve 40*a*, and through delivery line 36, such as line 36*a*. When line 36*a* is completely flushed, washer 26*a* is ready to receive a new product from mixing component 22. A one-way or check valve may be utilized as part of or in conjunction with valve 40*a* to prevent fluid from re-entry into manifold 34. A check valve may be provided on or at a location along delivery line 36*a*.

It may be appreciated that during the entire time of flushing line 36*a*, manifold 24 is utilized and is otherwise not available for dispensing product from product sources 28 to a different washing machine 26. Rather, in a typical central dispensing system, a device of such system, or an operator of such system, heretofore was required to wait until completion of the flushing of delivery line 36*a* before supplying a desired product to delivery lines 36*b*, 36*c*, . . . 36*n*, etc. and in turn to supplying product to the other washing machines 26*b*, 26*c*, 26*d*, . . . 26*n*, etc. Such extra waiting time is especially aggravated in cases where washing machine 26 is positioned a further distance from inlet manifold 24. For instance, if a washing machine 26*n* is located in a different room or zone of a building, the water flushed through manifold 24 must travel the increased distance to fully flush the delivery line 36*n* leading to machine 26*n*. This causes additional delay in freeing manifold 24 to supply product to a different washing machine 26. It may be appreciated that such delay results in poor quality and/or less efficiency of operation. For instance, chemical might not be delivered to a device until later in a cycle, which lessens chemical contact time with materials in the washer which reduces the quality of the wash, and/or cycle times may expand due to a machine waiting for a flushing or a dosing of product, thus taking longer to complete a cycle or series of cycles, and/or a dose may be missed altogether (or in part) such as when a programmed cycle or segment of a cycle times-out waiting for a signal. In some cases a wash cycle will be configured to skip a dose if a new dose request or other signal is received and will not go backwards to make a repeated attempt to supply a skipped dose. Further, in some instances an operator of a central dispensing system will load and start each washing machine 26 at the same time, i.e., a parallel start. In some instances two or more machines 26 will request chemicals or dosing, or complete a washing cycle, at or about the same time. Yet due to the delay in waiting for a full flush of the delivery lines 36, only one machine 26 will be flushed at a time. The added delay may result in skipping delivery of a dose or doses; or operators adjusting the cycle times or having incentive to otherwise expedite or adjust the flush timing of the system which may lead to further inefficiency or poor quality of washings. The present auxiliary flush mechanism, however, eliminates or reduces this waiting period and allows for supplying product to a different washer on a timely basis.

Figure 2:
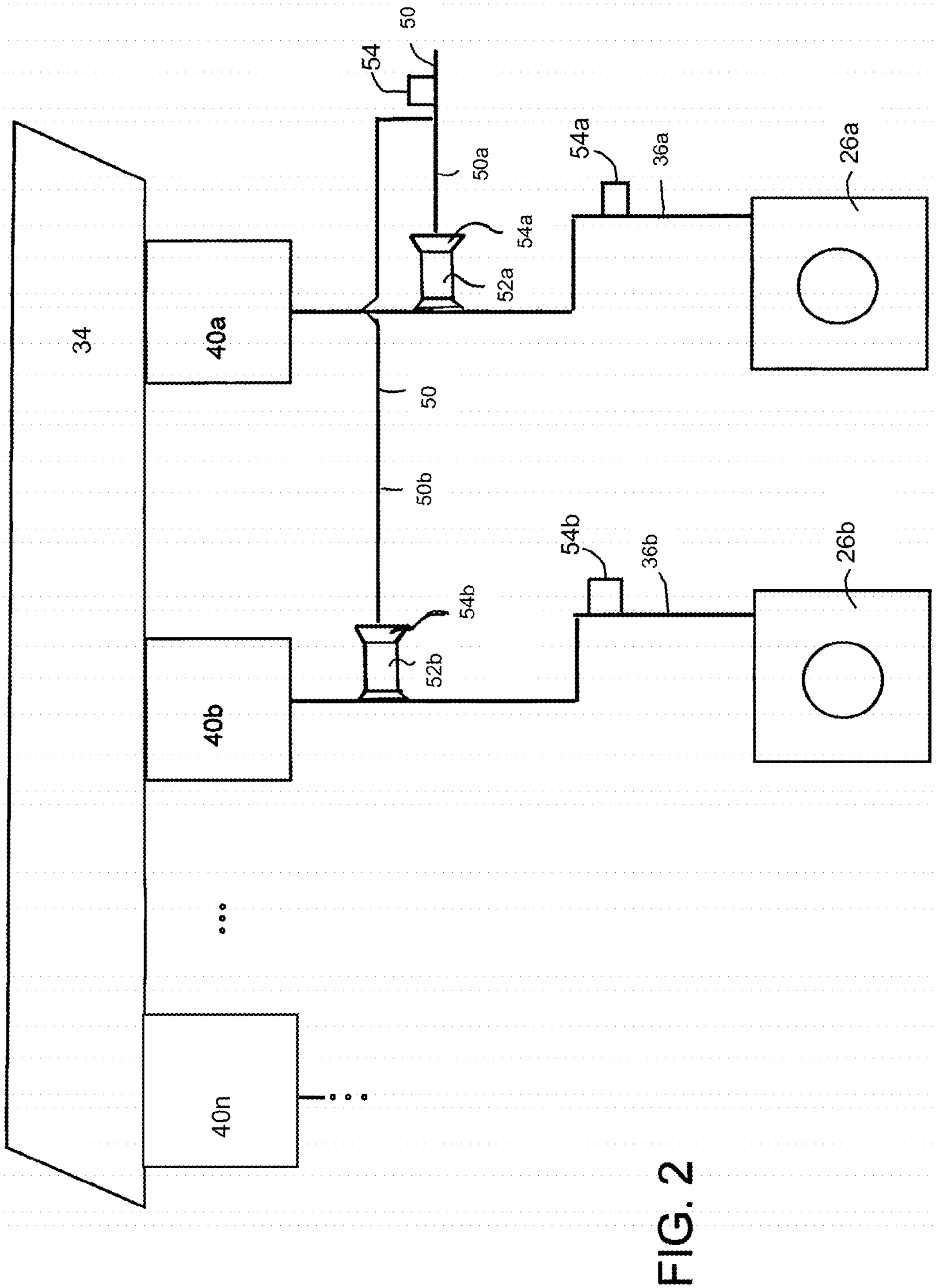
FIG. 2 illustrates schematically a close-up arrangement of a portion of the system of FIG. 1.

The supplemental or auxiliary flush mechanism of system 20 includes an auxiliary flush line 50. Flush line 50 provides liquid, such as water, to the washers 26 and delivery lines 36 for flushing. Flush line 50 is independent of or from manifold 24. In one aspect flush line 50 communicates with water supply 38 and delivers water to delivery line 36*a*. It may be appreciated that flush line 50 may receive a supply of water from an alternative source. As shown in FIG. 1 and FIG. 2, auxiliary flush valves 52 open and close to allow fluid to flow from flush line 50 to delivery lines 36. Particularly, in one aspect an auxiliary flush valve 52*a* will open to allow flushing water to flow from flush line 50/50*a* to delivery line 36*a*. A flush valve 52 may comprise a solenoid or other valve system, and may include a check valve or one-way valve. Auxiliary flow sensors 54 sense the flow of water through line 50 and valves 52. Particularly, flow sensor 54*a* senses the flow of water through flush line 50/50*a* which leads to delivery line 36*a* and to washer 26*a*. Similar flush lines 50/50*b*, 50*c*, etc. and flow sensors 54*b*, 54*c*, etc. may be used in conjunction with delivery lines 36*b*, 36*c*, etc. Alternatively and/or in addition to positioning flow sensors 54 on line 50 or 50*a*, for instance, flow sensors 54 may be positioned on delivery lines 36. In other aspects, it may be appreciated that a 3-way valve may be used with system 20. In one example a 3-way valve may be used to provide the same or similar operation performed by a product control valve 40 and an auxiliary flush valve 52. It may be appreciated that the schematic shown if FIG. 2 may be modified with a 3-way valve to replace the control valve 40*a* and flush valve 52*a*. A 3-way valve may also include one-way or check-valve characteristics. A flow sensor 52 may also be associated with the 3-way valve to sense flow of fluid before, during and/or after 3-way valve.

It may be appreciated that use of flush line 50 to flush delivery line 36*a* (associated with washer 26*a*) frees manifold 24 to provide product from product sources 28 to a different washer, such as to washer 26*b*. Particularly, product control valve 40*a* closes to prevent fluid from exiting outlet manifold 34 into delivery line 36*a*. Instead, flush line 50 supplies water to flush delivery line 36*a* and product control valve 40*b* (or other valve 40*c*, etc.) is free to open to supply product from manifold 34 which is received from inlet manifold 24. In this manner washer 26*b* may be supplied with products, such as detergent, bleach, etc., via manifold 24 (from product sources 28), while washer 26*a* is being flushed via flush line 50, rather than waiting for washer 26*a* to be otherwise flushed via manifold 24. Such flush mechanism increases the overall efficiency of system 20.

In one aspect of the operation, system 20 includes water supply 38 which may receive water from a pressurized water source or from a water supply reservoir or other source. Supply 38 provides water to manifold 24 via input liquid supply line 39. A water supply pump may supply water to inlet manifold 24. A manual shut-off maintenance valve 43 may allow for shut-off of water. An inlet manifold control valve 46 opens and closes to allow water to enter manifold 24. An inlet flow sensor 48 senses the flow of water to manifold 24. An inlet check valve 49 is included at manifold 24 to prevent or inhibit flow of water in a reverse direction. A plurality of product supply lines 29 supply product from sources 28 to manifold 24. A plurality of product supply check valves 31 are included at manifold 24 to prevent or inhibit flow of chemical product in a reverse direction.

System 20 further includes a controller 60. Controller 60 is equipped with program logic and devices to control and regulate the operation of system 20. Controller 60 communicates with the various sensors and valves and pumps to control and regulate flow of water and liquid products throughout system 20. In one aspect controller 60 includes direct electrical connection or communication with sensors 54, 48 and other sensors to determine the nature of flow conditions. Controller 60 also includes direct electrical connection or communication with valves such as product control valves 40, flush valves 52, manifold control valve 46, and pumps 30, 44. Controller may include electrical connection or communication with other devices as desired. In further aspects controller may include wireless contact or communication with the various components via send signals 62 and receive signals 64 from the various components which may be reciprocally equipped for such purposes. The controller may include logic circuits, storage medium, a processor, and other electrical arrangements for such controlling of the system. Timing and other control logic and warning and data collection aspects may be incorporated into the controller 60. Controller 60 may also control alarms associated with system 20, which may include among other aspects both audible and visual alarms to warn of various states (i.e., low or empty product sources 28 (receiving data from float switches or level sensors), invalid formula requests (in cases where pre-programmed formulas are not utilized or overridden by a user), incomplete delivery programs, incompatible product alarms, automatic shut offs, data flow indicators, temperature readings, etc. A monitor or display with input/output buttons, screen, touch screen or controls may also be used in conjunction with controller 60.

While system 20 includes pumps 30, it may be appreciated that an aspirator or aspirators may be used alternatively. For example, in one instance manifold 24 may be reconfigured so that flow of water from input line 39 creates a pressure or vacuum to draw in a product or chemical from product supply line or lines 29. Control valves may open/close to allow a desired product from lines 29 to be introduced into the manifold. The suction as water flows from input 39 past control nozzles within manifold 24 causes the fluid from product sources 28 to aspirate or travel into manifold 24. The dosing may be controlled by adjusting the flow pressure of inlet water or varying the sizes of nozzles, among other control adjustments.

Figure 3:
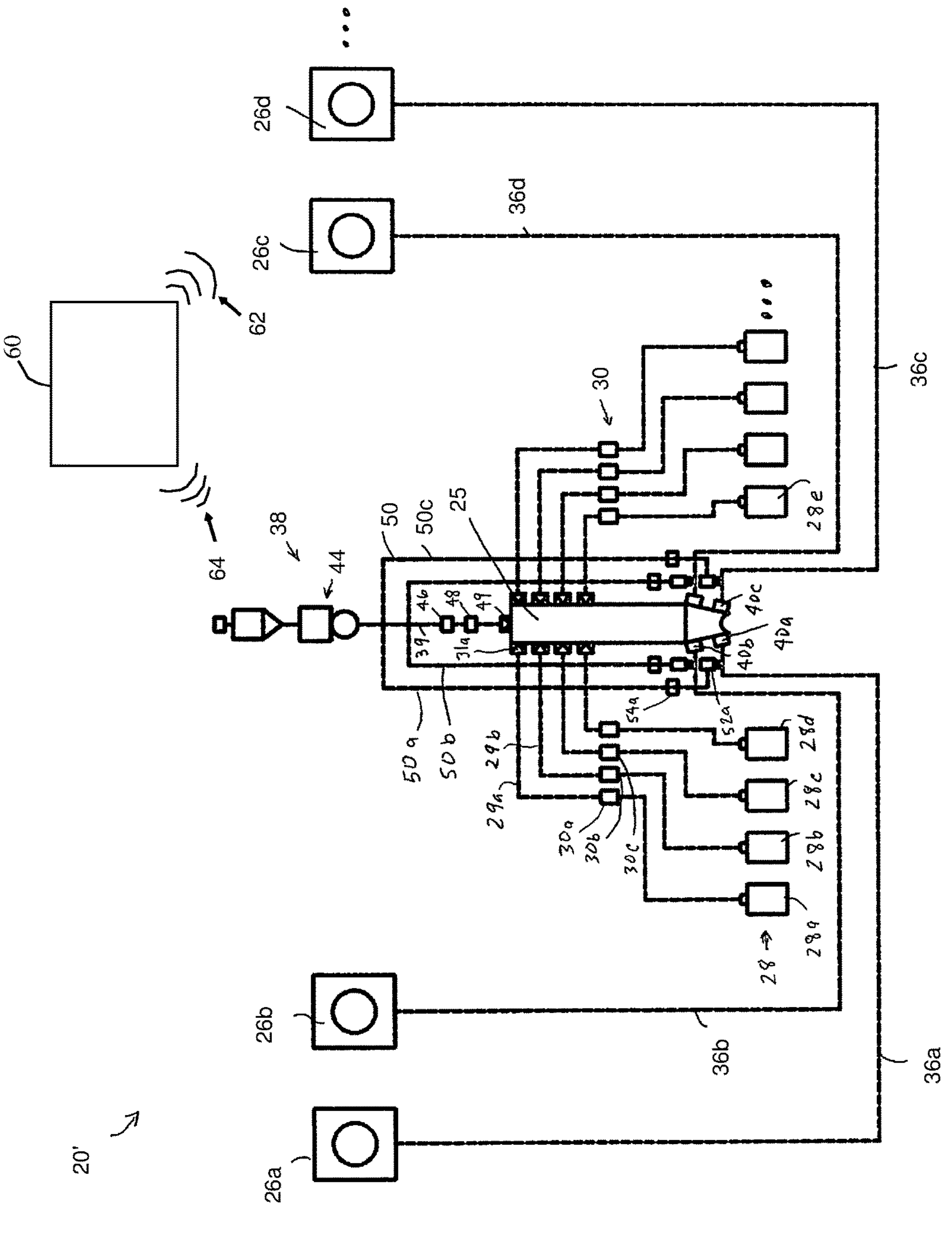
FIG. 3 illustrates schematically the arrangement of a central dispensing system in accordance with an alternative aspect of the present invention.

In a further aspect with respect to FIG. 3, control dispensing system 20' includes a manifold 25. Input liquid supply line 39 provides water to manifold 25. Product supply lines 29 supply products from product sources 28 to manifold 25. Product control valves 40 control the exit of chemical product from manifold 25 to delivery lines 36 to utilization devices 26. In one aspect utilization devices include washers 26. Auxiliary mechanism includes an auxiliary flush line 50 in fluid communication with delivery lines 36. Each supply line 36 is in communication with an auxiliary flush line 50, such as 50*a*, 50*b*, 50*c*, etc. Supply lines 29 include supply pumps 30 to pump chemical products to manifold 25. The system 20' operates similar to the system 20 yet includes a single manifold 25 to handle both the mixing of product(s) and dispensing of product(s) to respective delivery lines 36 of the utilization devices 26. A washer 26*a*, for instance, may undergo a flush from flush line 50*a* while washer 26*b*, for instance, may receive a product dose from manifold 25 (via opening of product control valve 40*b*). It may be appreciated that washers 26 may also receive a flush from manifold 25 via opening of product control valves 40 to deliver water from source 38 to washers 26. Utilizing auxiliary flush lines 50 reduces the cycle time of the entire system in the event multiple washers 26 are in queue for receiving a product dose and/or for flushing. It may be appreciated that multiple washers 26 may receive an auxiliary flush simultaneously. It may also be appreciated that a washer 26 may receive a dose while a different washer 26 is receiving a flush of water. A plurality of product supply check valves 31 (such as at valve 31*a*) are included at manifold 25 to prevent or inhibit flows in a reverse direction, i.e., from entering or reentering product supply lines 29 or sources 28.

Figure 4:
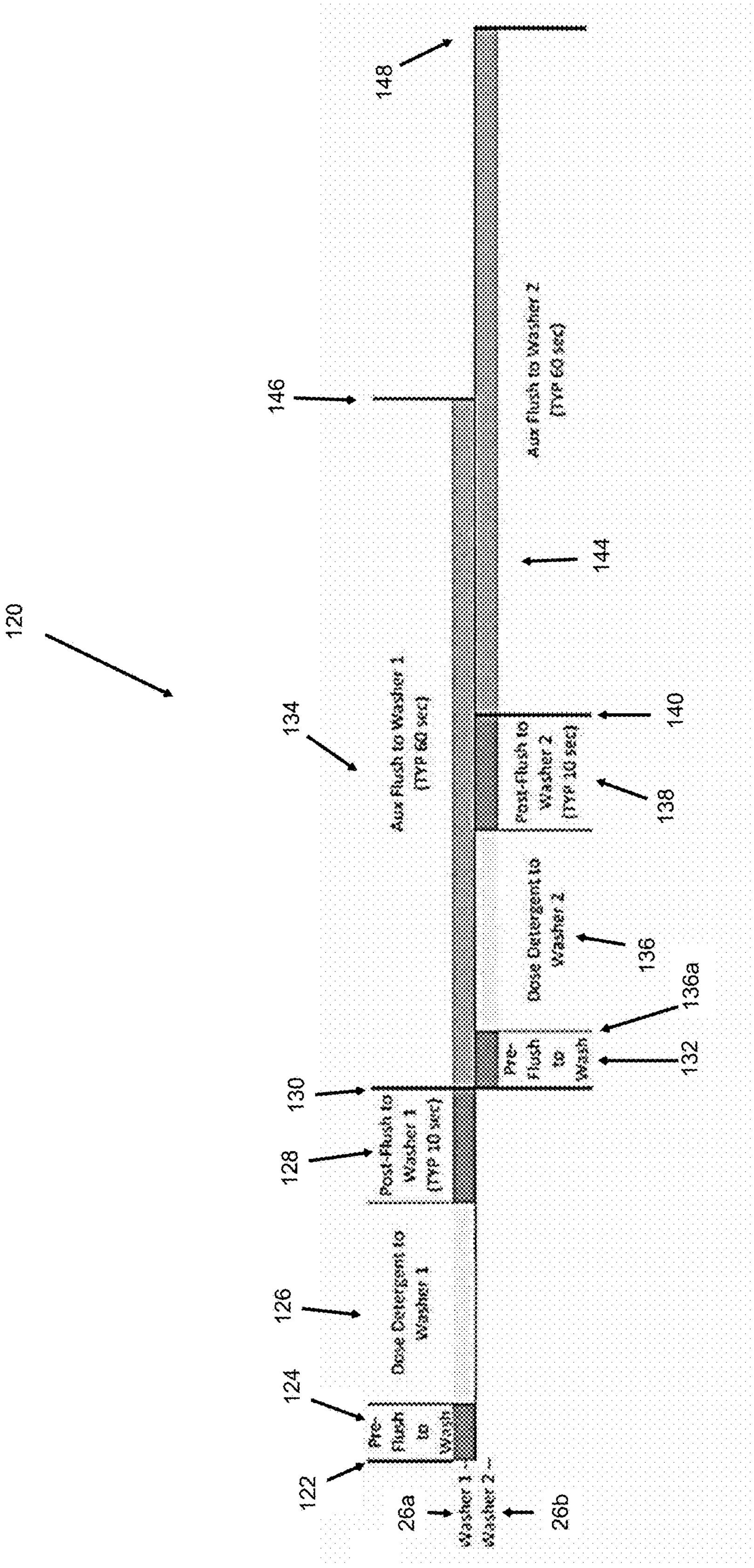
FIG. 4 is a timing diagram in accordance with aspects of the present invention.

In a further aspect of the invention, and in reference to FIG. 4, a method 120 of the invention includes a step at 122 of powering on product control valve 40*a* (see also FIG. 2) followed by a pre-flush of washer 26*a* at step 124. Step 124 may commence at or after powering on or opening valve 40. While times may vary, a typical pre-flush runs about 5 seconds. In one aspect the pre-flush 124 is achieved by delivering fluid through manifold 24 and through delivery line 36*a*. At step 126 product control valve 40*a* remains open and a dose of chemical product is delivered from manifold 24 (via products sources 28) to manifold 34 to delivery line 36*a* to washer 26*a*. The chemical product originates from product sources 28 (or one of the sources 28). The chemical product is mixed with water at manifold 24 (or may be pumped with or without additional mixing by running product supply pump 30). For instance, a product contained in product source 28 may be pumped into manifold 24 without also having water enter manifold 24 from line 39. It may be appreciated that product source 28 may also include water (or other material) to supply to manifold 24. It may also be appreciated that multiple products may be simultaneously delivered to manifold 24, for instance, by simultaneously activating multiple pumps 30. After the full dose is delivered, which delivery time may vary, a post-flush 128 is undertaken by running water through manifold 24, 34, and through delivery line 36*a* to washer 26*a* (while control valve 40*a* remains open). A post flush step 128, for instance, may typically last for 10 seconds. At step 130 control valve 40*a* closes which stops the post-flush operation. It may be appreciated that in one aspect washer valve 40 opens at step 122 and may remain open until step 130.

At step 130 control valve 40*b* may be opened to initiate a pre-flush operation on washer 26*b* (the timing path of washer 26*b* is generally represented by the events occurring below the baseline of the diagram). Valve 40*b* may open shortly after the closing of control valve 40*a*, with a one second delay or other delay, for instance. In one instance valve 40*b* may be opened simultaneously or nearly simultaneously with the closing of control valve 40*a*. The pre-flush period at step 132 may last a sufficient period of time to further assure the flushing of fluid through manifold 24, 34 and the delivery line 36*b*. In one instance the pre-flush period at step 132 may last about 5 seconds. Pre-flush 132 may end at a dosing start 136*a* which initiates a dosing period 136 where a dose of chemical product is delivered from manifold 24 to manifold 34 to delivery line 36*b* to washer 26*b*. Dosing start 136*a* begins with operation of product supply pumps 30. The chemical product originates from product sources 28 (or one of the sources 28). The chemical product is mixed with water at manifold 24. After the full dose is delivered, which delivery time may vary, a post-flush 138 is undertaken by running water through manifold 24, 34, and through delivery line 36*b* to washer 26*b* (while control valve 40*b* remains open). In one aspect washer control valve 40*b* may be closed (powered off) at step 140 and simultaneously or thereafter auxiliary flush 144 initiates to flush delivery line 36*b* and washer 26*b*. In this instance auxiliary flush line 50*b* is opened by activating auxiliary flush valve 52*b* (powered on). In this instance both delivery line 36*a* and delivery line 36*b* may simultaneously receive water from respective auxiliary flush line 50. Auxiliary flush of washer 26*a* may run a pre-set time, typically about 60 seconds. Such times may vary depending on the application. These times may be adjusted as desired. Auxiliary flush of washer 26*b* may also run a pre-set time, typically about 60 seconds, for instance. The duration of the flush time may vary depending on the desired application. Auxiliary flush 134 ends when flush valve 52*a* is powered off or closed at step 146. Auxiliary flush 144 ends when flush valve 52*b* is powered off or closed at step 148. It may be appreciated that the above method includes activating the auxiliary flush in order to flush the respective delivery lines 36 and respective washers 26. FIG. 4 also corresponds to a situation where washer 26*a* and washer 26*b* are started simultaneously, such as both washer requiring a dose of detergent. It may be appreciated that washer 26*b* must wait to receive the dose until after dosing is completed for washer 26*a*. Yet dosing of washer 26*b* may begin prior to a full flushing of washer 26*a* due to the present auxiliary flushing mechanism.

Figure 5:
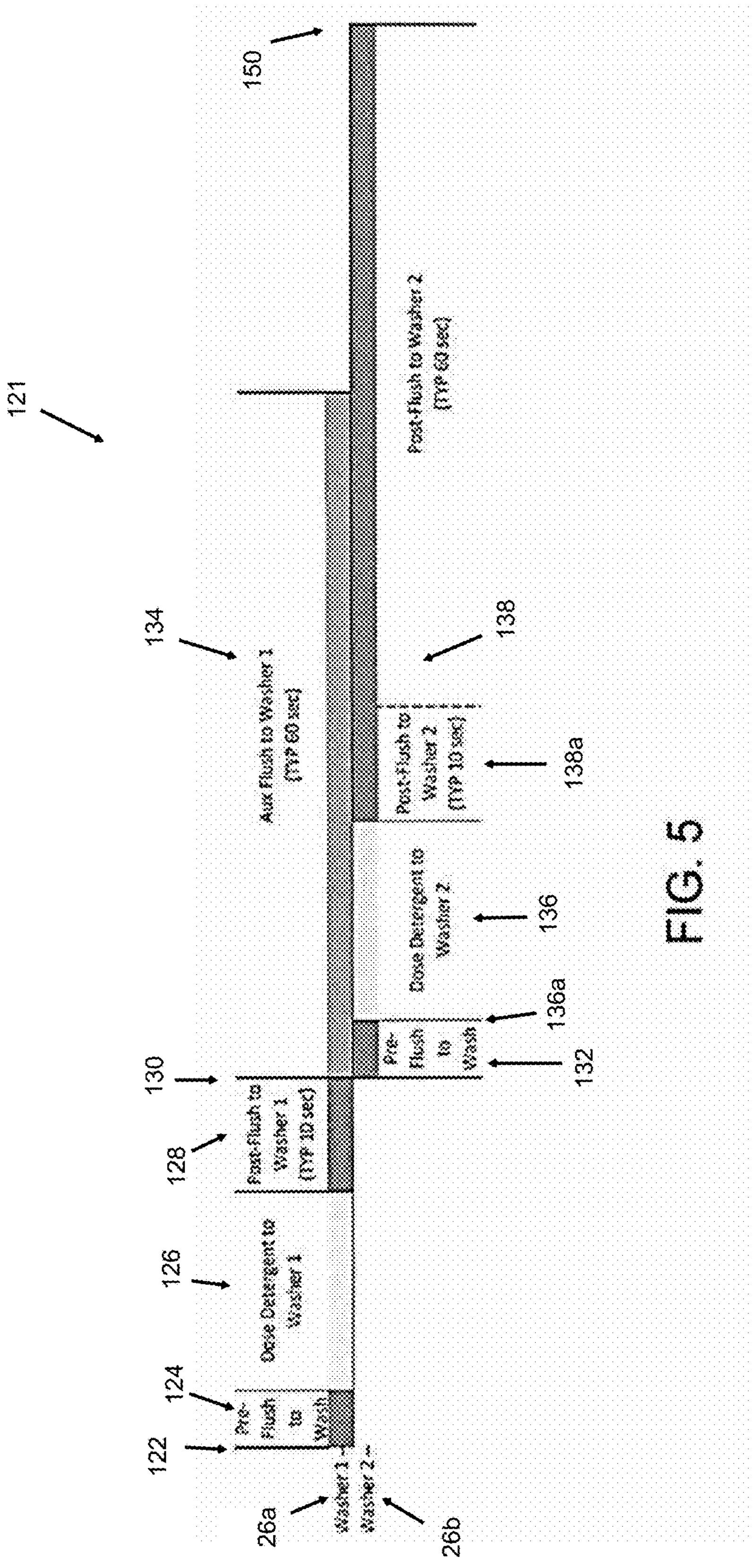
FIG. 5 is a timing diagram in accordance with further aspect of the present invention.

In a further method aspect 121 with respect to FIG. 5, it may be appreciated that an auxiliary flush is activated when a queue is present, such as when washer 26*a* receives an auxiliary flush, washer 26*b* does not receive an auxiliary flush since there is no further queue or other device or washer requesting or requiring a dose of chemical product. Instead, washer 26*b* receives an extended post-flush 138. Particularly, post flush 138*a*, which might typically last 10 seconds, may be programmed or allowed to run an additional 60 seconds to continue an extended post-flush 138 of washer 26*b*. In this method an auxiliary flush is not utilized for the second washer, such as washer 26*b*. The auxiliary flush step 134, however, is still utilized to speed the overall system since washer 26*b* may receive a dosing 136 without having to wait for washer 26*a* to receive a length post-flush (typically 10 seconds plus 60 seconds). At step 150 washer valve 40*b* is powered off or closed which stops the post-flush step 138.

It may be appreciated that in a case of a third washer requesting a chemical product dose, such as washer 26*c*, the system 20 and method 120 may utilize a further auxiliary flush step which may run simultaneously with the auxiliary flush step 134, 144 of FIG. 4 and/or simultaneously with the auxiliary flush 134 and/or post-flush 138 of FIG. 5. It may be appreciated that further washers 26 and auxiliary flush steps may be utilized where multiple dosing steps are frequently requested and in order to shorten the overall time to supply the doses to the respective devices or washers.

It may be appreciated that an auxiliary flush step 134, 144 may be used to substantially shorten the overall dosing operation of system 20, 20', 20" and methods 120, 121 where a washer 26*n* is positioned a relatively remote or long distance from manifold 24, 34. In a case where several washers 26 are positioned proximal manifold 24, 34, such washers 26 receive a post-flushing during a relatively short duration as compared to a washer 26*n* positioned a remote or distal location from manifold 24, 34. For instance, if washer 26*a*, washer 26*b* and washer 26*c* are located approximately 10 feet from manifold 34, the respective flush and dosing times are generally equivalent among the washers 26*a*, 26*b*, 26*c*. Where a washer 26*n*, however, is positioned in a different room or location remote from washers 26*a*, 26*b*, 26*c* or remote from manifold 34, for instance a distance of 50 feet or more (distances may vary), the flush duration will be much greater due to the increased travel distance of the fluid and due to the requirement to supply additional water to fill the lines. Further, during a dosing interval, the dosed product must travel a greater distance, and therefore, requires a greater amount of water to push the dose to the machine in order to fill the line leading to the washer 26*n*. If there is no auxiliary flush mechanism or flush line 50 to supply the water, then manifold 34 would otherwise be used to continue the supply of water to accompany the dose to machine 26*n*, thus delaying use of manifold 34 for other deliveries. It may be appreciated that auxiliary flush mechanism and flush line 50 (or individual lines 50*a*, 50*b*, etc.) are used to supply water so that a dose may be delivered to washers 26 which frees manifold 34 for additional and simultaneous use. In one aspect, the auxiliary flush mechanism operates as an auxiliary dose delivery system (i.e., to push the dose to a washer). The controller is configured to control the various differences in terms of length of delivery lines 36 and balance the amount of product and water which passes through the various lines over different times. In the case of supplying a dose to a remote washer 26*n*, the subsequent post-flush will take a relatively long period of time to be completed. When a different washer 26, such a proximal washer 26*a* requires a dose of product, and without the assistance of the present auxiliary line flushing, the proximal washer 26*a* must nonetheless wait until the conclusion of the post-flushing of remote washer 26*n*. With the subject invention which utilizes auxiliary flush line 50, the manifold 24, 34 may be utilized for delivering a dose to proximal washer 26*a* (by powering valve 40*a* to be open and closing valve 40*n* while also opening auxiliary flush valve 52*n*). In this instance it may be appreciated that simultaneous flushing of washer 26*n* and dosing of washer 26*a* shortens the overall waiting time of the systems 20, 21 and methods 120, 121.

Figure 6:
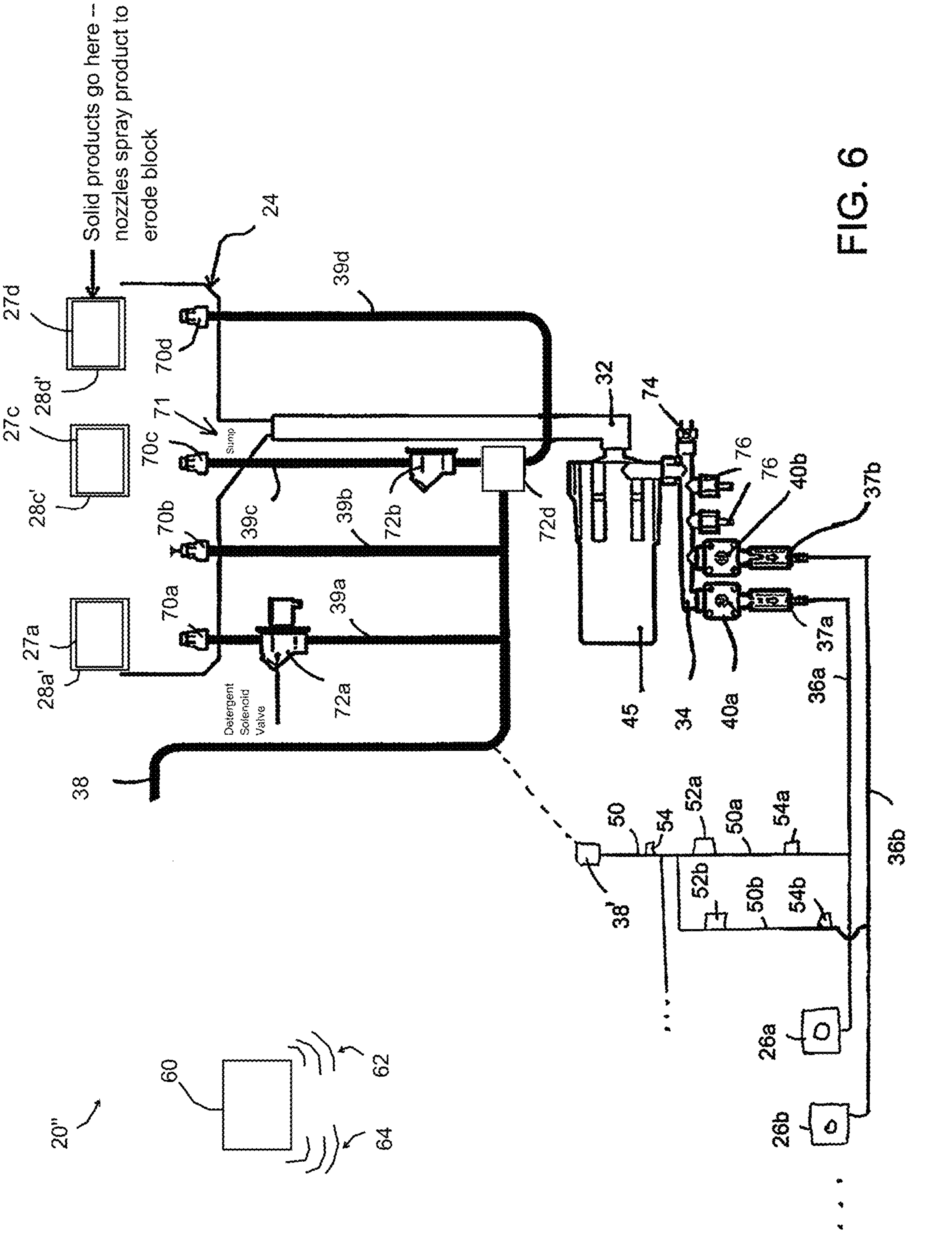
FIG. 6 illustrates schematically the arrangement of a central dispensing system in accordance with an alternative aspect of the present invention.

In a further aspect of the invention and with reference to FIG. 6, a central dispensing system 20" which utilizes a solids dispensing system is generally shown. Water supply 38 provides water to product sources 28'. At sources 28' are disposed solid products, such as a product blocks 27. A block 27*a* may be a detergent, for instance, while other blocks may include different materials or compositions, including but not limited to a bleach block 27*c* or sour/softener block 27*d*, or other solids. Water from nozzles 70 is sprayed upon the respective blocks 27 to dissolve or release a desired amount of the product. Dissolved product, liquid, slurry or other material is released from product sources into mixing tank or manifold 24 which operates as a sump 71 to funnel or deliver the product to transport line 32. Line 32 may be a hose configured to collect the product material and liquid. Sump 71 or manifold 24 may be made of plastic or other desired material.

It may be appreciated that a nozzle 70, such as nozzle 70*b* may be configured to supply a water spray as a flush of manifold 24 (i.e., in one aspect nozzle 70*b* is configured with a top or cap to direct water for flushing, as opposed to directing water toward a product source 28*b*'. Valves 72 are provided to open/close or otherwise deliver water from input liquid supply line 39*a* to nozzles 70. Valves 72 may include solenoid valves. A normally open/normally closed valve 72*d* may be used, or other varieties of valves may be used, to assure some products are not dispensed with other products. Valve 72*d* may include an electrical component or solenoid aspect to control operation of valve 72*d*. It may be appreciated that valve 72*d* may be a three-way valve. A main solenoid valve may be arranged with water supply 38 to open and close flow of water through supply 38. It may be appreciated that valve 70*b* may configured to remain open (where water to valve 70*b* is controlled by turning on/off the supply to line 38 such as with a main solenoid valve) in which case valve 70*b* operates as a pre-flush, helps with a dosing/flush, and operates as a post flush.

Fluid or product mixture from manifold 24 travels to transport line 32 and then pumped to outlet manifold 34 by pump 45. Product control valves 40 are provided at outlet manifold 34 to control delivery of the product to respective devices or washers 26. Typically only one control valve 40 may be opened at a time.

As product and fluid exits control valve 40, such as exits control valve 40*a*, it travels through delivery line 36*a* to washer 26*a*. A check valve 37*a* is provided to assure one-way flow away from manifold 34. Pump 45 activates to pump the product and fluid to washer 26*a* for a dosing step. It may be appreciated that pump 45 may be stopped, valve 40*a* closed, and the dosing may continue by providing water through auxiliary flush line 50 to washer 26*a*. Particularly, water travels through flush line 50*a* which is in communication with line 36*a* to push the product/dose from within line 36*a* to washer 26*a*. In this manner the manifold 34 and pump 45 are available for use with a different washer 26*b* or other washer 26*n*. It may be appreciated that utilizing auxiliary flush line 50*a* speeds the timing for supplying a dose to a different washer.

Flush line 50*a* includes a flush valve 52*a*. A flush sensor 54 may be included on each flush line 50 so that the flow to each particular washer 26*a* may be detected. Alternatively, or in addition to placing sensors 54 on lines 50*a*, 50*b*, 50*c*, etc., an auxiliary flow sensor 54 may be positioned on main flush line 50 at a position before the individual flush lines 50*a*, 50*b*, etc. A controller 60 is provided to receive and send signals and to control the operation of system 20". Each of the electronic elements of system 20" may be wired to controller 60 (or alternatively configured for wireless communication as desired). Controller 60 is programmed to send and receive data or electrical signals and control operation of system 20".

Flush line 50 may receive water from a water supply 38', which may be a water supply which is independent from water supply 38. Alternatively, or in addition to being an independent water supply, supply 38' may be connected to water supply 38 as represented by the dotted line on FIG. 6. It may be appreciated that supply 38, 38' may include various control devices, quages, regulators, strainers, tanks, pressure supplies, pumps, etc. configured to supply the water to system 20". It may be appreciated that the methods described herein with respect to systems 20, 20' may also be used with solid product dispensing system 20". It may be appreciated that opening of a product control valve 40 by itself will not necessarily provide a supply of product to lines 36. Typically pump 45 will need to be activated to create a pressure to supply the product to lines 36. It may be appreciated that auxiliary flush mechanism and flush line 50 may be used as both a dosing delivery system and a post flush system.

It should be understood, of course, that the foregoing relates to exemplary embodiments of the invention and that modifications may be made without departing from the spirit and scope of the invention as set forth in the following claims. The scope of this invention also includes embodiments having different combinations of features and embodiments that do not include all of the above described features.

What is claimed is:

1. A central dispensing system comprising:

an inlet manifold configured to receive at least a first product;

an outlet manifold in fluid communication with said inlet manifold through a connecting line;

a first delivery line extending from the outlet manifold and connected to a first washer;

a second delivery line extending from the outlet manifold and connected to a second washer; and an auxiliary flush line connected to at least one of said first delivery line and second delivery line, wherein the outlet manifold comprises:

a first control valve configured to control flow of product from said outlet manifold through the first delivery line to the first washer, and a second control valve configured to control flow of product from said outlet manifold through the second delivery line to the second washer, and wherein the auxiliary flush line is configured to provide a liquid to at least one of said first delivery line and second delivery line.

2. The system of claim 1 further comprising an auxiliary flush flow sensor associated with said auxiliary flush line.

3. The system of claim 1 further comprising a flush valve associated with said auxiliary flush line and configured to open to allow fluid to flow from said auxiliary flush line to said first delivery line.

4. The system of claim 1 where said auxiliary flush line provides a liquid to said second delivery line, said system further comprising an auxiliary flush flow sensor and a flush valve associated with said auxiliary flush line and configured to allow fluid to flow to said second delivery line.

5. The system of claim 4, wherein said auxiliary flush line is configured to provide water to said first delivery line while said second delivery line receives product from said outlet manifold.

6. The system of claim 1 where said inlet manifold is configured to receive a first liquid product and a second liquid product and further comprising an input liquid supply line configured to supply liquid from a water supply to said inlet manifold, and an inlet control valve configured to open to allow water to flow to said inlet manifold.

7. The system of claim 6 further comprising a water flush flow sensor associated with said auxiliary flush line and an inlet flow sensor associated with said input liquid supply line.

8. The system of claim 7 where said system further comprising a controller configured to communicate with said inlet flow sensor and said water flush flow sensor.

9. The system of claim 8 further comprising a first liquid product supply line in communication with said inlet manifold and at least a second liquid product supply line in communication with said inlet manifold, each product supply line having a product supply pump in communication with said controller which is configured to control operation of said pumps.

10. The system of claim 1 where said inlet manifold includes a sump and where nozzles associated with solid product sources are oriented within said inlet manifold and configured to spray water to dissolve products, a transport line connected to a pump and configured to receive the dissolved products from said inlet manifold, said pump configured to pump the dissolved products to said outlet manifold.

11. The system of claim 1, wherein the auxiliary flush line bypasses at least one of the inlet manifold and the outlet manifold.

12. A central dispensing system comprising:

a manifold configured to receive an input supply and a first product, said manifold having a first product control valve configured to allow flow of product from said manifold through a first delivery line to a first utilization device, and at least a second product control valve configured to allow flow of product from said manifold through at least a second delivery line to at least a second utilization device; and a first auxiliary flush line in fluid communication with said first delivery line and a second auxiliary flush line in fluid communication with said second delivery line.

13. The dispensing system of claim 12 further comprising multiple product receptacles each having an associated supply pump configured to supply liquid product from a respective receptacle to said manifold, and further comprising multiple delivery lines each in fluid communication with a respective utilization device, each delivery line configured to receive fluid from said manifold through a respective product control valve and each delivery line configured to receive water from said auxiliary flush line through a respective auxiliary flush valve.

14. The dispensing system of claim 13 further comprising a controller configured to receive data from flow sensors associated with respective auxiliary flush lines and to operate said respective auxiliary flush valves, said controller further configured to power a product control valve simultaneously with powering an auxiliary flush valve.

15. A central dispensing system comprising:

an inlet manifold configured to receive at least one product and to provide the product through a connecting line to an outlet manifold for delivery through at least a first delivery line to a first washer and through a second delivery line to a second washer, a product control valve associated with each of said first and second delivery lines and configured to allow flow of product from said outlet manifold to the first washer and the second washer; and each of said first delivery line and said second delivery line in fluid communication with a respective auxiliary flush line, each respective auxiliary flush line having an auxiliary flush valve configured to allow flow of water from said respective auxiliary flush line to the first delivery line or the second delivery line, said first delivery line configured to receive flush water from a respective said auxiliary flush line while said second delivery line simultaneously receives product from said outlet manifold.

16. The system of claim 15 further comprising a controller configured to control said respective auxiliary flush valves and said respective product control valves.

17. A method for use with a central dispensing system which includes a manifold for providing a variety of products to multiple washers, said method comprising:

dosing a first washer of the central dispensing system with a product received from the manifold; and after said step of dosing the first washer, flushing the first washer with a liquid through an auxiliary flush line bypassing the manifold while simultaneously dosing a second washer of the central dispensing system with a product received from the manifold.

18. The method of claim 17 where said step of flushing the first washer is achieved by utilizing an auxiliary flush line independent of the manifold.

19. The method of claim 18 further comprising flushing the second washer utilizing the auxiliary flush line.

20. The method of claim 18 further comprising simultaneously flushing the first washer and the second washer utilizing the auxiliary flush line while simultaneously dosing a third washer of the central dispensing system with a liquid product received from the manifold.

21. The method of claim 17 further comprising post-flushing the first washer after said step of dosing with fluid from the manifold and pre-flushing the second washer with fluid from the manifold after post-flushing the first washer, said simultaneous dosing occurring after pre-flushing the second washer.

* * * * *